United States Patent

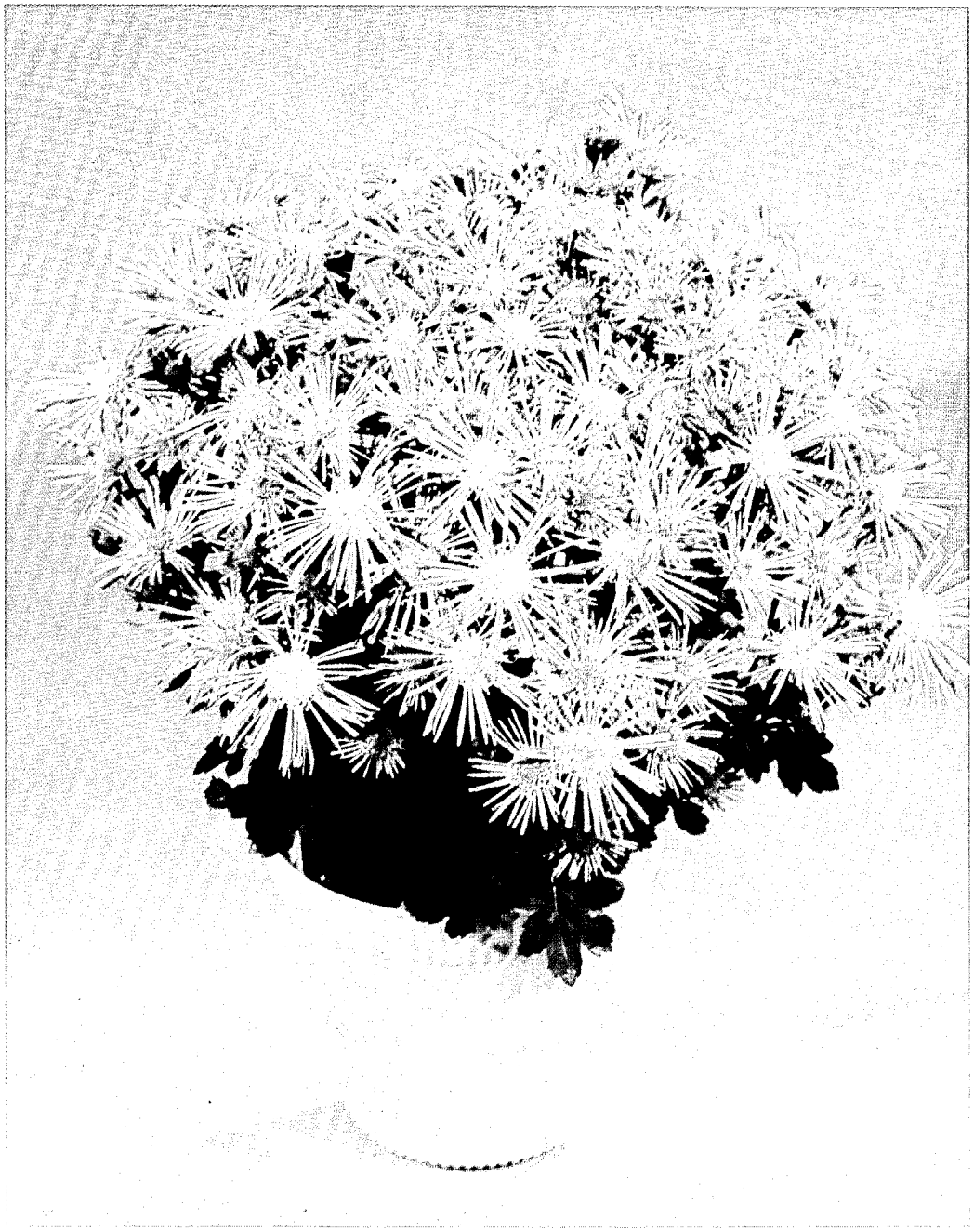

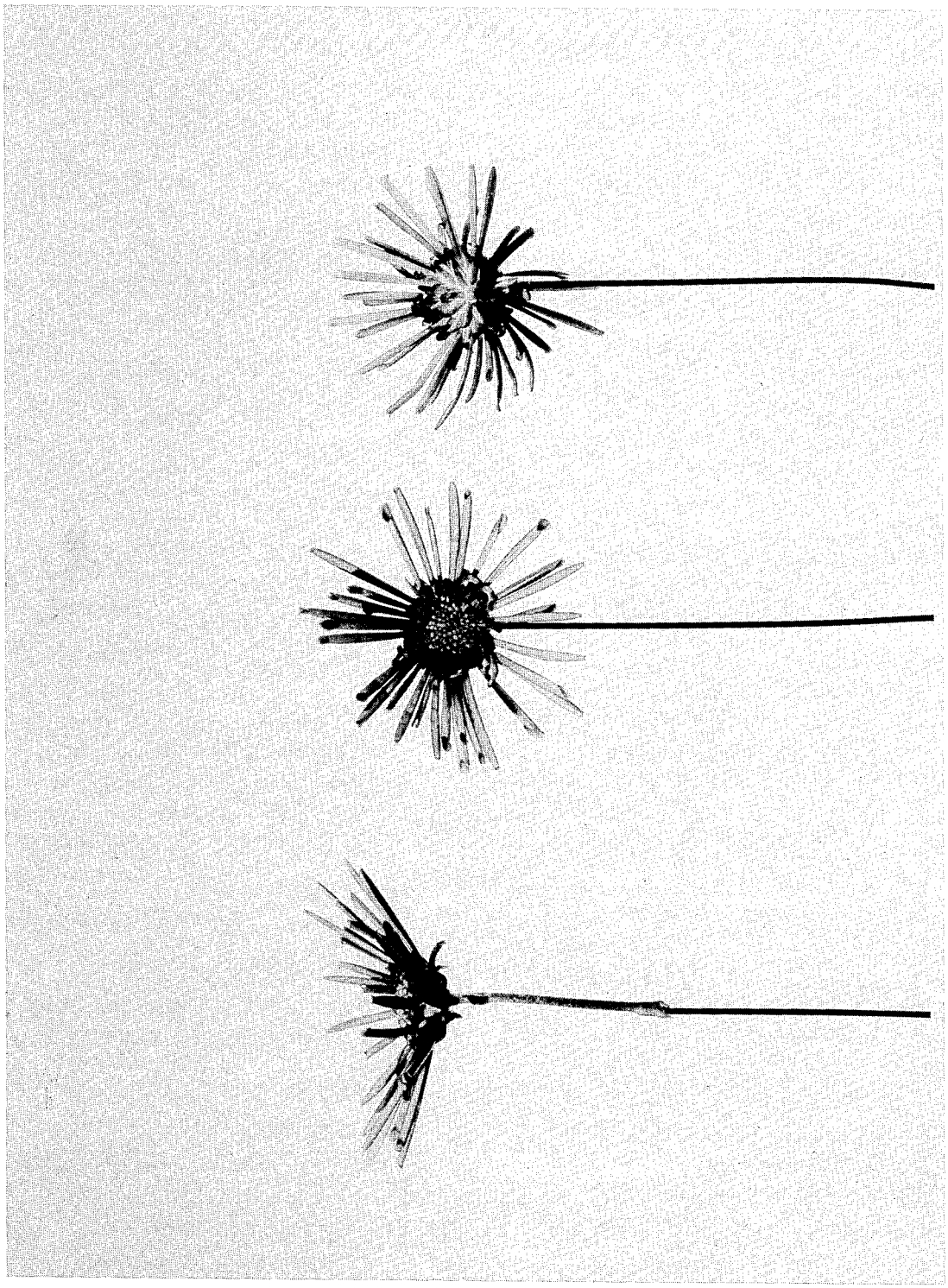

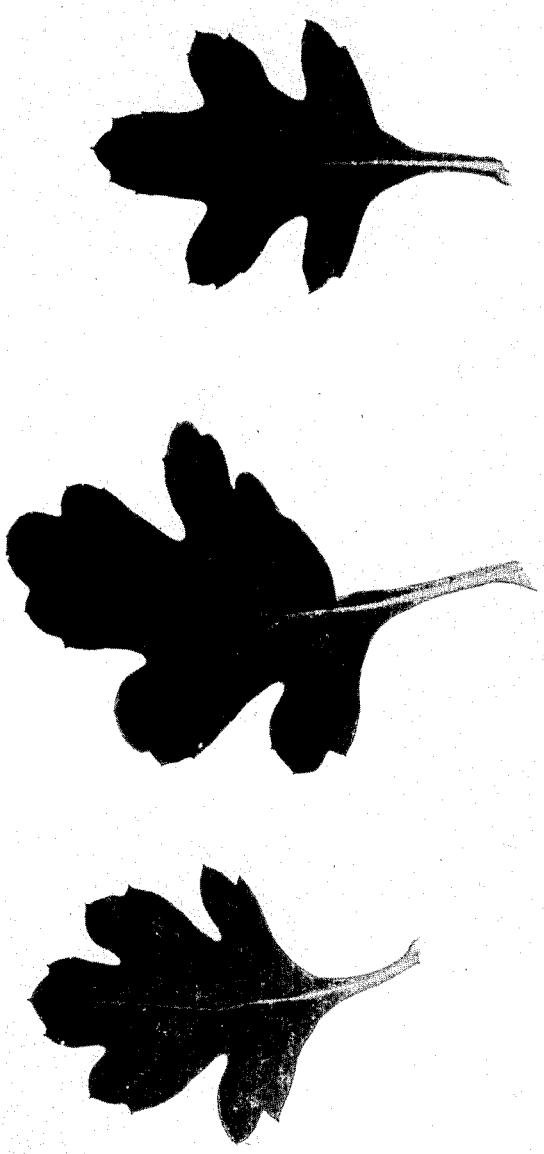

Plant Pat. 3,933

Patented July 6, 1976

3,933

CHRYSANTHEMUM PLANT

Walter H. Jessel, Jr., Doylestown, and William E. Duffett, Akron, Ohio, assignors to Yoder Brothers, Inc., Barberton, Ohio Filed June 11, 1975, Ser. No. 585,861

Int. Cl.[2] A01H 5/00

U.S. Cl. Plt.—74 1 Claim

The present invention comprises a new and distinct cultivar of *Chrysanthemum morifolium*, Ramat., hereinafter referred to by the cultivar name Liberty (#73217004).

Liberty was originated from a cross made in a controlled breeding program in Barberton, Ohio in the year 1972. The female, or seed parent, was #72030006 (unnamed seedling), a light pink spooned daisy originated by the present inventors from a self-pollination of #70010002 (unnamed seedling). The male, or pollen parent of Liberty, was #72033006 (unnamed seedling), a lavender pink spooned daisy originated by the present inventors from a cross between #70010002 (unnamed seedling) and #70026002 (unnamed seedling). Both #70010002 and #70026002 were products of the breeding program of the present inventors.

Liberty is a product of a planned breeding program which had the objective of creating cultivars with novel inflorescence types of pink and lavender-pink color for natural season outdoor culture, early response, spreading branching pattern, and prolific flowering traits. These traits in combination were not present in previously available commercial cultivars.

Liberty was discovered and selected as a flowering plant within the progeny of the stated cross by William E. Duffett and Walter H. Jessel, Jr. on May 1, 1973 in an outdoor field in Fort Myers, Fla.

The first act of asexual reproduction of Liberty was accomplished when vegetative cuttings were taken from the initial selection in June 1973 in a controlled environment in Barberton, Ohio by a technician working under formulations established and supervised by William E. Duffett and Walter H. Jessel, Jr. Horticultural examination of selected units initiated Oct. 23, 1973 has demonstrated that the combination of characteristics as herein disclosed for Liberty are firmly fixed and are retained through successive generations of asexual reproduction.

Liberty has not been observed under all possible environments. The phenotype may vary significantly with variations in environment such as temperature, light intensity, and daylength. The following observations, measurements, and comparisons describe plants grown in a field in Barberton, Ohio under outdoor environmental conditions which are generally described in Local Climatological Data, Annual Summary With Comparative Data, Akron, Ohio. U.S. Department of Commerce, National Oceanic and Atmospheric Administration, Environmental Data Service, Washington, D.C., 1973, 1974 and Tables of Sunrise, Sunset, and Twilight. Supplement to The American Emphemeris, 1946. U.S. Naval Observatory, Washington, D.C., p. 103. When an environment divergent from that described was utilized to more clearly define a trait, that environment is specified.

The following traits have been repeatedly observed and are determined to be basic characteristics of Liberty which in combination distinguish this chrysanthemum as a new and distinct cultivar:

(1) Lavender pink inflorescence color.
(2) Flat inflorescence form, not known to reflex at maturity.

(3) Spoon-anemone inflorescence type.
(4) Tall plant height.
(5) Spreading branching pattern.
(6) Six-week flowering response in controlled programs.
(7) Average natural season flower date of September 20.
(8) Diameter across face of inflorescence from 2.25 to 3.0 inches at maturity.

The accompanying photographic drawings show typical inflorescence and foliage characteristics of Liberty, with the colors being as nearly true as possible with illustrations of this type. Sheet 1 is a color photograph of Liberty. Sheet 2 is a black and white photograph showing three views of the inflorescence of Liberty. Sheet 3 is a black and white photograph of the foliage of Liberty at three stages of growth.

Of the many commercial cultivars known to the present inventors, the most similar existing cultivars in comparison to Liberty are Stardom (#68324M01; U.S. Plant Pat. No. 3,530) and Muted Sunshine (#21630E04; unpatented).

Reference is made to attached Chart A which compares certain characteristics of the abovementioned cultivars with the same characteristics of Liberty. General comparisons are as follows:

(1) In comparison to Stardom, Liberty has different inflorescence color and type, taller plant height, earlier average natural season flower date, and larger diameter across face of inflorescence. The inflorescence form, branching pattern, and controlled flowering response of Liberty are similar to those of Stardom.

(2) In comparison to Muted Sunshine, Liberty has different inflorescence color and type, taller plant height, later average natural season flower date, and smaller diameter across face of inflorescence. The inflorescence form, branching pattern, and controlled flowering response of Liberty are similar to those of Muted Sunshine.

In the following description, color references are made to The Munsell Limit Color Cascade, 1972 edition. The color values were determined between 2:30 and 3:00 p.m. on April 8, 1975 under 150 foot-candle light intensity in Barberton, Ohio.

Botanical classification: *Chrysanthemum morifolium*, Ramat., cv Liberty.

I. INFLORESCENCE

A. *Capitulum*
- *Form:* flat.
- *Type:* spoon-anemone.
- *Permanence:* 14 to 18 days.
- *Diameter across face:* 2.25 to 3.0 inches.

B. *Corolla of ray florets.*
- *Texture:* glabrous.
- *Appearance and form:* tubular.
- *Arrangement:* whorled on receptacle.
- *Persistence:* resists shatter.
- *Color (abaxial):* approximately 45–8 to 45–13.
- *Color (adaxial):* approximately 45–3 to 42–15.

C. *Corolla of disc florets*
- *Appearance and form:* gameopetalous; elongated; tubular; 5-lobed.
- *Color:* approximately 45–8 to 45–13 over 23–11 to 27–4.

D. *Reproductive organs*
- *Androecium:* abundant; present disc florets only; syngenesious stamen; abundant pollen.
- *Gynoecium:* present both ray and disc florets; inferior, bicarpellate ovary; single style; 2-lobed ovary.

II. PLANT

A. *General appearance:* spreading; tall.
B. *Duration and texture:* herbaceous; perennial.
C. *Foliage*
*Color (abaxial):* 21–15 overlaid with white.

*Color (adaxial):* 21–13 overlaid with white.
*Shape:* spatulate; moderately lobed.
*Texture:* glabrous; leathery.
*Arrangement:* alternate.
*Veination:* prominent.
*Margin:* moderately serrated.

CHART A.—COMPARISON OF LIBERTY, STARDOM, AND MUTED SUNSHINE

| Cultivar | Inflorescence color | Inflorescence form and type | Plant height | Natural season flower date | Branching pattern | Controlled flowering response | Diameter across face of inflorescence |
|---|---|---|---|---|---|---|---|
| Liberty | Lavender pink | Flat spoon anemone | Tall | Sept. 20 | Spreading | 6 weeks | 2.25 to 3.0 inches. |
| Stardom | Pink | Flat daisy | Short | Sept. 25 | do | do | 1.75 to 2.25 inches. |
| Muted Sunshine | Yellow | Flat anemone | do | Sept. 15 | do | do | 3.0 to 4.0 inches. |

NOTE.—Comparisons made of plants grown under natural season outdoor field conditions in Barberton, Ohio.

We claim:

1. A new and distinct cultivar of chrysanthemum characterized particularly by the combined characteristics of lavender-pink inflorescence color, flat inflorescence form which is not known to reflect at maturity, spoon-anemone inflorescence type, tall plant height, spreading branching pattern, six week flowering response in controlled programs, average natural season flower date of Sept. 20, and 2.25 to 3.0 inches diameter across face of inflorescence at maturity.

No references cited.

ROBERT E. BAGWILL, Primary Examiner